(12) United States Patent
Wieskotten et al.

(10) Patent No.: US 11,224,682 B2
(45) Date of Patent: Jan. 18, 2022

(54) PERITONEAL DIALYSIS MACHINE

(71) Applicant: FRESENIUS MEDICAL CARE DEUTSCHLAND GMBH, Bad Homburg (DE)

(72) Inventors: Sebastian Wieskotten, Erfelden (DE); Peter Zeyher, Darmstadt (DE); Florian Guenther, Freiburg (DE); Klaus Wolf, Arnstein-Muedesheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 15/752,141

(22) PCT Filed: Aug. 9, 2016

(86) PCT No.: PCT/EP2016/001364
§ 371 (c)(1),
(2) Date: Feb. 12, 2018

(87) PCT Pub. No.: WO2017/025186
PCT Pub. Date: Feb. 16, 2017

(65) Prior Publication Data
US 2018/0236155 A1 Aug. 23, 2018

(30) Foreign Application Priority Data
Aug. 11, 2015 (DE) .................... 10 2015 010 431.4

(51) Int. Cl.
*A61M 1/16* (2006.01)
*A61M 1/28* (2006.01)
(Continued)

(52) U.S. Cl.
CPC ............ *A61M 1/1652* (2014.02); *A61M 1/28* (2013.01); *A61M 5/1415* (2013.01); *A61M 5/1418* (2013.01); *F16M 11/08* (2013.01); *F16M 11/10* (2013.01); *A61M 2209/082* (2013.01); *F16M 2200/022* (2013.01); *F16M 2200/024* (2013.01)

(58) Field of Classification Search
CPC .... A61M 1/28; A61M 5/1415; A61M 5/1418; A61M 1/1652; A61M 2209/082; F16M 11/08; F16M 11/10; F16M 2200/021; F16M 2200/022; F16M 2200/024; Y10T 403/32008; Y10T 403/32041
USPC ........... 248/229.1, 70, 73, 51, 52, 67, 278.1, 248/274.1, 276.1, 685, 686, 253, 550; 16/230, 231, 232, 259, 270
See application file for complete search history.

(56) References Cited

U.S. PATENT DOCUMENTS 1,800,349 A * 4/1931 Hurason ................... B25G 3/38
                                                                 403/57
4,529,352 A * 7/1985 Suzuki ................... B23K 9/287
                                                                 248/201
(Continued)

FOREIGN PATENT DOCUMENTS

EP             2682139          1/2014

*Primary Examiner* — Kimberly T Wood
(74) *Attorney, Agent, or Firm* — Jacobson Holman PLLC

(57) ABSTRACT

A peritoneal dialysis machine has at least one mount for fixing one or more sections of a hose set for conducting a dialysis solution from and/or to a patient. A first pivot axle is provided about which the mount can be pivoted from a first position into a second position.

8 Claims, 3 Drawing Sheets

(51) Int. Cl.

*A61M 5/14* (2006.01)
*F16M 11/08* (2006.01)
*F16M 11/10* (2006.01)

(56) References Cited

U.S. PATENT DOCUMENTS

| | | | | |
|---|---|---|---|---|
| 4,705,243 | A * | 11/1987 | Hartmann | B23K 11/362 248/160 |
| 4,767,257 | A * | 8/1988 | Kato | B25J 19/0025 285/190 |
| 4,770,377 | A * | 9/1988 | Callaway | F16L 3/00 24/132 AA |
| 4,820,274 | A * | 4/1989 | Choksi | A61M 5/1418 128/DIG. 26 |
| 5,240,092 | A * | 8/1993 | Eachus | B25J 19/0025 191/12 R |
| 5,279,486 | A * | 1/1994 | Harmon | A61G 7/075 248/122.1 |
| 5,502,859 | A * | 4/1996 | Kim | A46B 5/0075 15/144.1 |
| 5,581,838 | A * | 12/1996 | Rocco | A46B 5/0075 132/309 |
| 5,720,040 | A * | 2/1998 | Simone | G02C 3/02 2/10 |
| 6,431,018 | B1 * | 8/2002 | Okada | B25J 19/0025 248/229.22 |
| 6,887,214 | B1 * | 5/2005 | Levin | A61M 1/3639 210/645 |
| 7,837,167 | B2 * | 11/2010 | Hartwig | A61M 5/1417 248/299.1 |
| 7,905,855 | B2 | 3/2011 | Childers | |
| 8,103,155 | B2 * | 1/2012 | Dannenberg | A45D 20/12 392/381 |
| 9,163,752 | B2 * | 10/2015 | Radakovic | F16L 3/015 |
| 10,376,626 | B2 * | 8/2019 | Jensen | A61G 7/0503 |
| 2005/0263661 | A1 * | 12/2005 | Park | A42B 1/247 248/292.12 |
| 2009/0179364 | A1 * | 7/2009 | Haley | B23K 3/087 269/9 |
| 2009/0187138 | A1 * | 7/2009 | Lundtveit | A61M 1/16 604/29 |
| 2009/0212178 | A1 | 8/2009 | Westberg | |
| 2009/0299273 | A1 | 12/2009 | Lee et al. | |
| 2010/0140149 | A1 * | 6/2010 | Fulkerson | A61M 1/14 210/85 |
| 2012/0123322 | A1 | 5/2012 | Scarpaci et al. | |
| 2013/0119209 | A1 * | 5/2013 | Radakovic | F16L 3/015 248/70 |
| 2013/0312644 | A1 * | 11/2013 | Copeland | A47B 21/0314 108/96 |
| 2014/0014786 | A1 | 1/2014 | Lucke | |
| 2014/0097303 | A1 | 4/2014 | Lake | |
| 2014/0259837 | A1 * | 9/2014 | Belliveau | A61M 5/1415 40/673 |
| 2015/0297826 | A1 * | 10/2015 | Slaker | A61M 5/1418 248/560 |
| 2018/0236153 | A1 * | 8/2018 | Zeyher | A61M 1/28 |

\* cited by examiner a)

b)

PERITONEAL DIALYSIS MACHINE

BACKGROUND OF THE INVENTION

1. Field of the Invention

The present invention relates to a peritoneal dialysis machine having at least one mount for fixing one or more sections of a hose set for conducting dialysis solution from and/or to the patient.

2. Description of Related Art

It is known with peritoneal dialysis machines known from the prior art to provide a mount at the machine e.g. for parts of a hose set, for receiving connectors or closing caps or for receiving patient connection lines, etc. Within the framework of a peritoneal dialysis therapy, for example, the patient thus has to connect the patient connection line to a receiving apparatus of the peritoneal dialysis machine under aseptic conditions.

It is known for this purpose to use a receiver, i.e. a so-called organizer, in which e.g. the connector of a patient connection line can be fixed so that the patient can establish a fluid connection using only one hand.

When inserting the hose or the connector into the mount of the peritoneal dialysis machine, forces, in particular vertical forces, occur which have to be absorbed by that part of the machine connected to the mount. A large torque which can result in damage to the housing of the peritoneal dialysis device, which typically comprises plastic, in this respect in particular arises for the case that the mount is arranged at a lever which is comparatively long.

SUMMARY OF THE INVENTION

It is therefore the underlying object of the present invention to further develop a peritoneal dialysis machine of the initially named kind such that damage to the machine and in particular to the machine housing is avoided even when comparatively large forces or torques arise on the mount.

This object is achieved by a peritoneal dialysis machine having the features described herein. Provision is accordingly made that at least one first pivot axle is provided about which the mount is pivotable from a first position into a second position.

The advantage can thereby be achieved that if a specific force or a specific torque is exceeded, the mount is pivoted from a first position into a second position and the forces or torques acting on the housing are thus reduced. The first pivot axle thus satisfies the object of a security against overload which prevents damage to the housing or to another element of the peritoneal dialysis machine at which the mount is arranged.

In a preferred embodiment of the invention, the peritoneal dialysis machine has at least one element which is preferably the machine housing, with the mount being arranged directly at this element and with the first pivot axle being located at the element or at the housing respectively.

However, the case is also covered by the invention that the peritoneal dialysis machine has an element or a housing and that the mount is not directly fastened thereto, but is rather fastened indirectly via at least one holder. In this case, the first pivot axle can be located between the holder and the mount and/or between the holder and the element or the machine housing.

It is ensured in all cases that the mount "evades" forces which are too high in that it is pivoted about the first pivot axle when specific forces or torques are exceeded.

The first pivot axle preferably extends horizontally or substantially horizontally. Other orientations of the first pivot axle are also conceivable and covered by the invention. It is important that the first pivot axle allows an evasion of the mount on forces or torques which are too large and thus prevents damage to the element of the machine to which the mount is connected.

In a further embodiment of the invention, the mount is aligned horizontally or substantially horizontally in its first, i.e. non-pivoted, position. Starting from this position, it can be pivoted by means of the first pivot axle into an e.g. vertical position or a position directed obliquely downwardly.

Provision is made in a further embodiment of the invention that the peritoneal dialysis machine has at least one element, preferably at least one housing, at which at least one second pivot axle is located which preferably does not extend in parallel with the first pivot axle and about which the mount or a holder connected to the mount is pivotable. It is thus possible to rotate the mount about this second pivot axle, e.g. from a region next to the housing in front of the housing.

This second pivot axle can extend vertically or substantially vertically. Other orientations of the second pivot axle are also conceivable and covered by the invention.

The second pivot axle is preferably arranged beneath the machine housing.

To ensure that the mount is only pivoted from the first position into the second position on an exceeding of a specific force or torque acting thereon, holder means can be present which are configured such that they only allow a pivoting into the second position when the force acting on the mount or the torque acting thereon exceeds a limit value.

It is avoided in this manner that an undue force acts on the mount or on the holder, e.g. from above, which is transferred to the machine housing in the non-pivoted position.

The named holder means can be at least two parts which are connected to one another by a force-transmitting or shape-matched connection or also one or more magnets.

A folding mechanism in the form of hinges, magnets or latch apparatus can, for example, be provided so that the organizer or the mount can flip downwardly.

It is pointed out at this point that the term "pivot axle" covers any desired mechanism, one-part or multi-part, having one or more pivot axles, about which the mount can be pivoted or folded down. Examples include the use of one or more bolts which are received in bearings, a lever mechanism, projections which are received in recesses, etc. A film hinge is also conceivable and also covered by the invention.

BRIEF DESCRIPTION OF THE DRAWINGS

Further details and advantages of the invention will be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
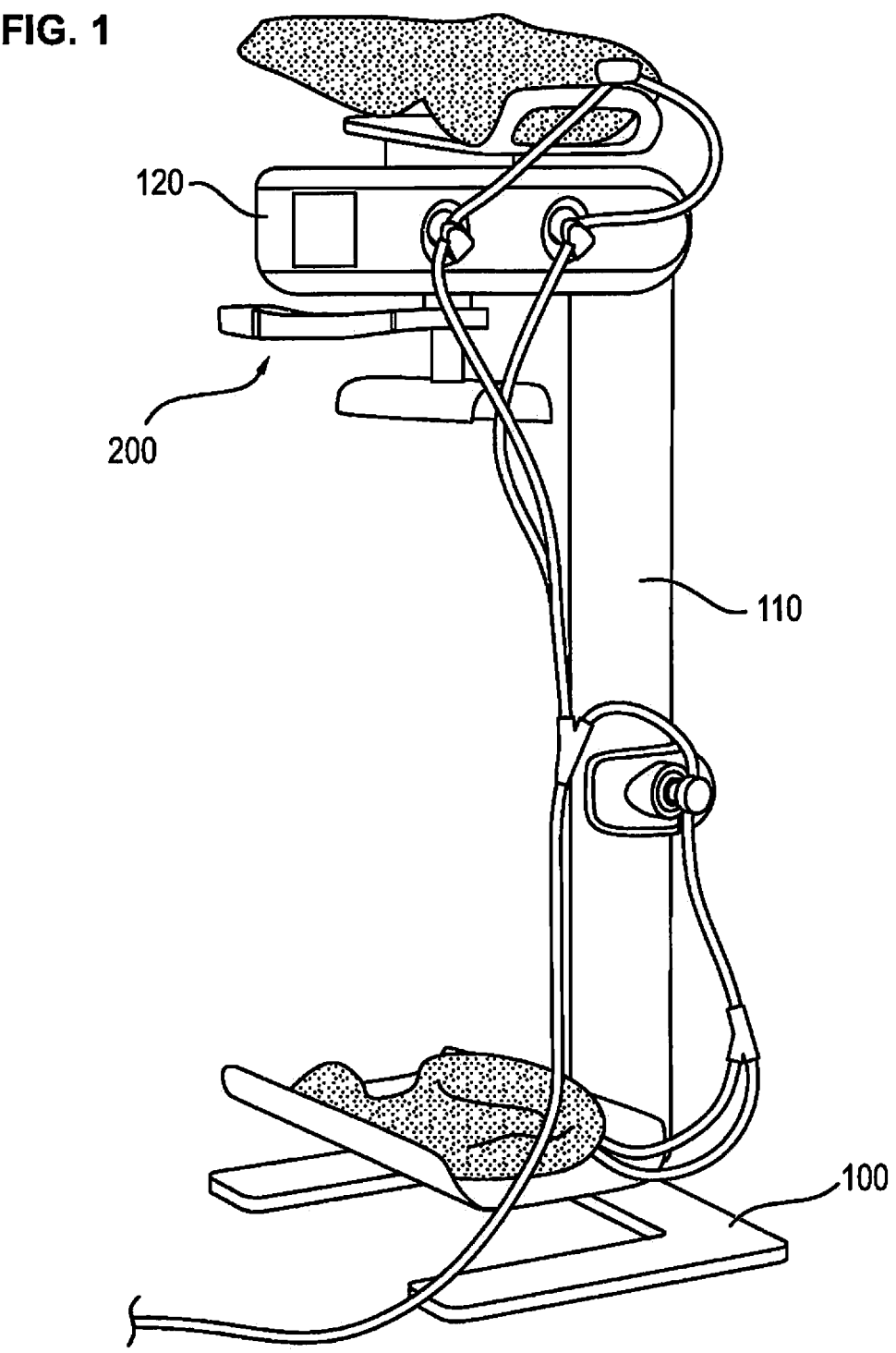
FIG. 1: a perspective view of a peritoneal dialysis machine in accordance with the invention.

FIG. 1 shows a peritoneal dialysis device in accordance with the invention in a perspective view.

The machine has a machine stand 100 as well as a housing carrier 110 extending upwardly therefrom. Reference numeral 120 marks the machine housing which is arranged at the housing carrier 110. The control required for the operation of the housing and optionally display and/or operating elements are arranged in the machine housing 120.

A weighing pan is located above the machine housing 120 and solution bags with the dialyzate to be administered can be placed into it.

The reception pan in which bags are arranged which are filled with consumed dialyzate is located beneath the machine housing 120 and directly above the stand 100.

Reference numeral 200 marks an arrangement which comprises the mount in accordance with the invention which will be described in more detail in the following.

Figure 2:
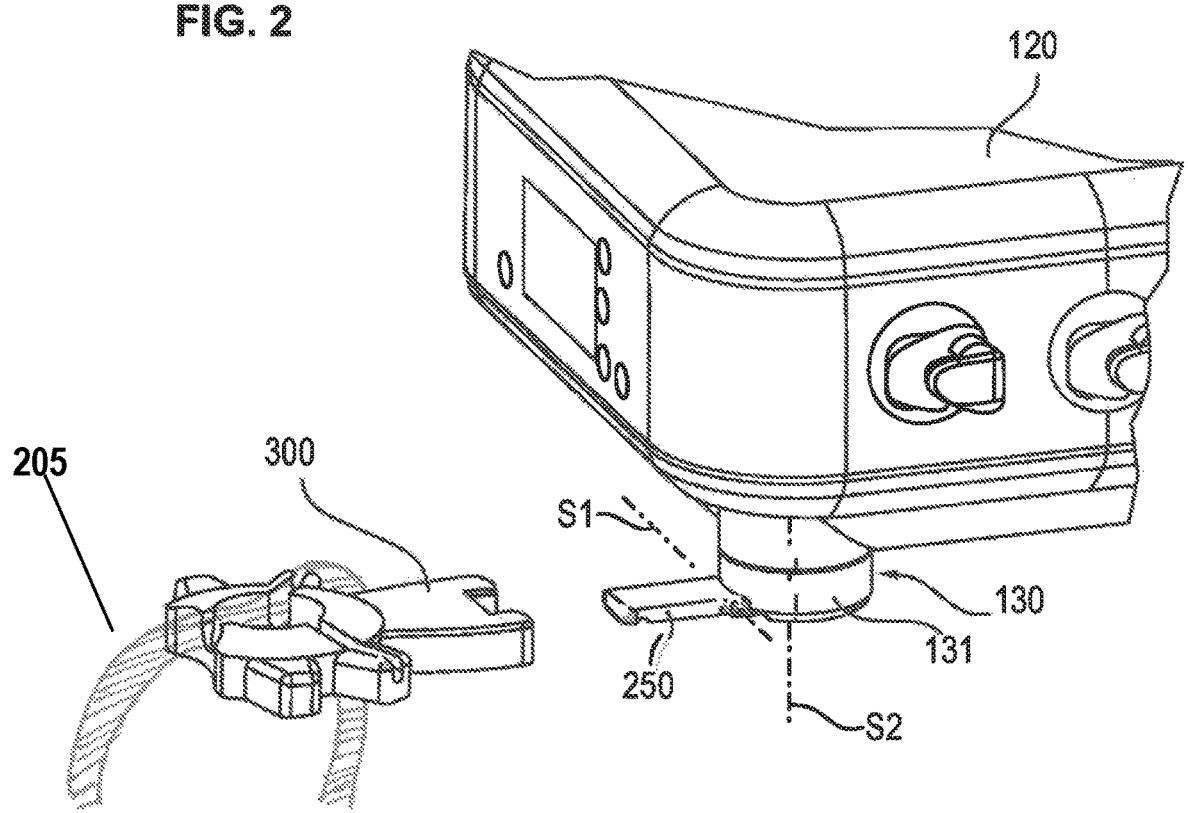
FIG. 2: a detailed view of the housing with a holder and a mount.

FIG. 2 shows a part section of the machine housing 120.

As can be seen from FIG. 2, a projection 130 whose lower part is formed by an element 131 that is rotatable about the vertical pivot axle S2 relative to the housing 120 is located in a corner region on the lower side of the machine housing.

The holder 250 is located at this element 131. The holder 250 extends away from the element 131 in a horizontal direction in the position shown in FIG. 2.

The holder 250 is pivotable about a horizontally extending first pivot axle S1 relative to the element 131.

The mount 300, which is also called an organizer in the following, is connectable to this holder 250 by force transmission or shape matching, for example. This organizer serves the reception of one or more components of a hose set of a peritoneal dialysis machine. This includes, for example, the hoses themselves and also connectors for connecting two hose sections.

It is thus conceivable, for example, that this mount is used to connect the hose which is connected to the dialysis bag to the patient hose which leads into the abdominal cavity. For this purpose, connectors can be provided at both ends which are preferably arranged in a shape-matched manner in the mount 300 so that the patient only needs one hand to establish a corresponding fluid connection.

The mount is generally not restricted to precisely this use, but can rather accept any desired suitable element of a hose set of a peritoneal dialysis machine.

It is pointed out at this point that the present invention protects the peritoneal dialysis machine per se, i.e. without hose set, and also a peritoneal dialysis machine in which such a hose set is located.

As has already been stated above, the holder 250 is arranged pivotably beneath the machine housing 120. It can thus, for example, be rotated from a position in which it faces in a direction next to the housing 120 to the front. The organizer or the mount 300 can e.g. be rotated to a position in front of the housing, i.e. in accordance with FIG. 2 to the front, for loading with the disposable and also during the treatment.

If the mount 300 is now loaded with elements of the hose set, such as with a connector, forces act on the mount 300, generally from above.

These forces are then transmitted via the holder 250 onto the element 131 and from this onto the housing 120. In this respect, undue introductions of force into the housing 120, which typically comprises plastic, can occur and said housing may then be damaged.

To avoid such damage, provision is made that the mount or the holder 250 is arranged pivotably at the housing 120. If an unduly large force presses onto the mount 300 from above, the holder 250 with the mount 300 is pivoted downwardly and thus evades. The organizer thus flips downwardly.

Instead of a simple pivot axle, any desired other folding mechanism, lever mechanism or other mechanism can also be used to allow such a downward flipping or pivoting of the mount 300.

Figure 3:
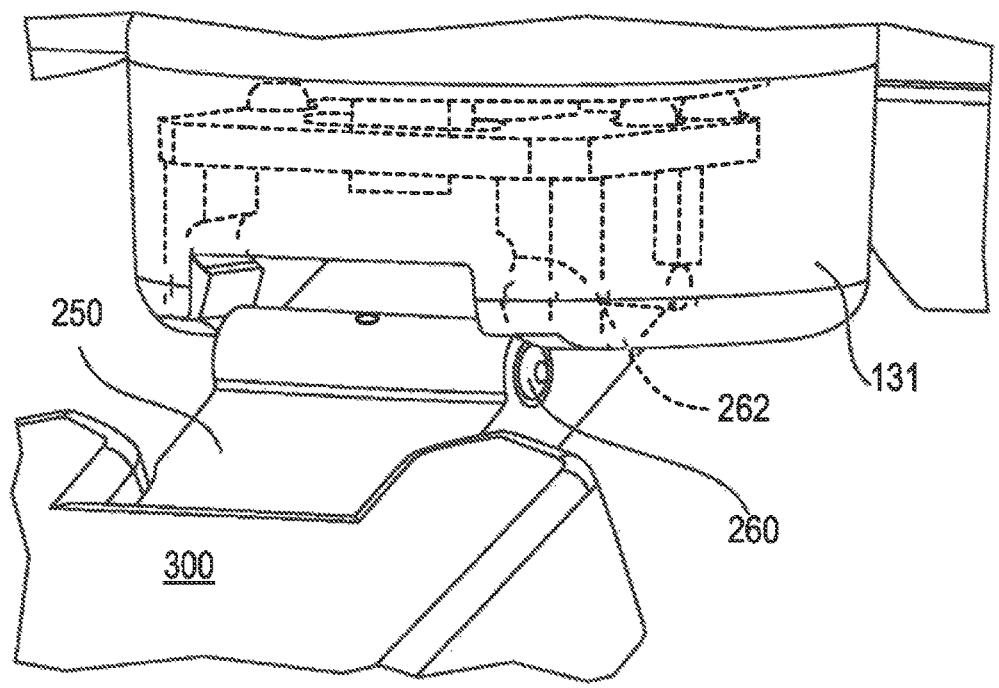
FIG. 3: a further detailed view of the housing with a holder and a mount.

FIG. 3 shows a detailed representation of the element 131 which is rotatable about the second pivot axle S2 relative to the housing. The holder 250, such as was shown n FIG. 2, is arranged pivotably about the first pivot axle S1 at this element 131.

To prevent an unwanted downward pivoting of the holder 250 and thus also of the organizer 300, a holding mechanism is provided which can be designed, for example, in the form of a latching apparatus. Reference numeral 260 in FIG. 3 marks a spring-loaded piston, sphere or other projection which is pressed into a corresponding receiver 262 in the first position of the mount. If the force acting on the mount exceeds a specific limit value, the piston 260 etc. is pressed in against the spring force, whereupon the holder 250 can be pivoted downwardly.

Figure 4:
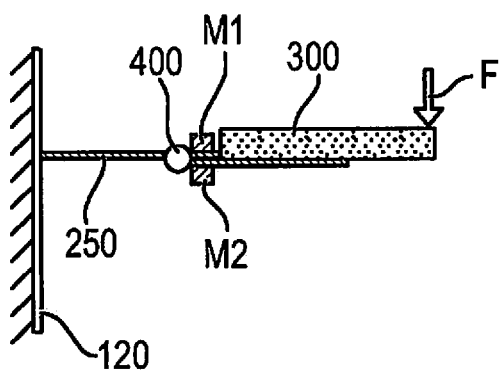
FIG. 4: a schematic view of the arrangement in accordance with the invention in the first position and in the second position of the mount.
Figure 4:
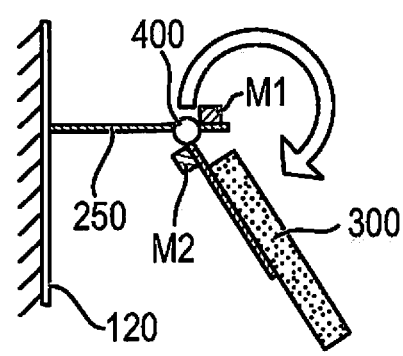

FIG. 4 shows a further embodiment of such a holder mechanism.

The housing of a peritoneal dialysis machine is marked schematically by reference numeral 120 in FIG. 4.

The holder 250 extends in the horizontal direction in front of it. A hinge 400 about which the mount 300 can be downwardly pivoted from the first position in accordance with FIG. 4 a) into the second position in accordance with FIG. 4 b) is located at the region or end region of the holder 250 facing away from the housing 120. This is indicated by the arrow in accordance with FIG. 4 b).

In the embodiment in accordance with FIG. 4, the fixing of the mount 300 in the first position, i.e. in the horizontal position, is not established by a latching connection, but rather by the magnets M1 and M2, with one magnet M1 being arranged at the holder 250 and the other magnet M2 being arranged at the mount 300 pivotable relative thereto.

In the first position of the mount in accordance with FIG. 4 a), the magnetic force is sufficient to hold the mount 300 in the position shown.

If the force F becomes too large, it exceeds the magnetic force, whereupon the mount 300 is pivoted downwardly.

It is ensured, independently of the precise mechanism of the pivoting or flipping downward of the mount 300 by a pivot axle, by hinges, etc., that forces or torques which are too high and which act on the mount 300 are not transmitted to the housing 120 or are only transmitted in reduced form. The probability of the occurrence of damage to the machine and in particular to the machine housing is thus reduced.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A peritoneal dialysis machine comprising:
a hose set for conducting a dialysis solution at least one of to a patient, and from the patient;
a mount into which one or more sections of the hose set is insertable;
a holder, which connects the mount to a rotatable element disposed at a housing of the peritoneal dialysis machine, the holder being pivotable about a first pivot axle from a first position, in which the holder is oriented to project horizontally outward from the rotatable element, to a second position, in which the holder is oriented in a vertical or substantially vertical position, and the rotatable element being rotatable about a second pivot axle which does not extend in parallel with the first pivot axle; and
a latching apparatus, which retains the holder in the first position to prevent an unwanted downward pivoting of the holder, and which only allows a pivoting of the holder from the first position to the second position upon an application of a force to the holder or to the mount connected to the holder that exceeds a force associated with the insertion of the one or more sections of the hose set into the mount.

2. The peritoneal dialysis machine in accordance with claim 1, wherein the first pivot axle is arranged horizontally or substantially horizontally.

3. The peritoneal dialysis machine in accordance with claim 1, wherein the mount is aligned horizontally or substantially horizontally in the first position.

4. The peritoneal dialysis machine in accordance with claim 1, wherein the second pivot axle extends vertically or substantially vertically.

5. The peritoneal dialysis machine in accordance with claim 1, wherein at least one of the first pivot axle and the second pivot axle is arranged beneath the rotatable element.

6. The peritoneal dialysis machine according to claim 1, wherein the element at which the second pivot axle is arranged is a projection from the housing.

7. The peritoneal dialysis machine according to claim 1, wherein the latching apparatus includes a spring-loaded piston and a receiver for the spring-loaded piston.

8. The peritoneal dialysis machine according to claim 7, wherein in the first position of the holder, the spring-loaded piston is press-fit into the receiver, and upon the application of the force to the holder or to the mount connected to the holder, the piston is pushed in against the spring force so as to release the piston from the receiver and enable the holder to pivot downward to the second position.

* * * * *